US00PP24891P2

(12) United States Plant Patent
Groot

(10) Patent No.: US PP24,891 P2
(45) Date of Patent: Sep. 16, 2014

(54) POINSETTIA PLANT NAMED 'PER2009'

(50) Latin Name: ***Euphorbia pulcherrima* Willd.**
Varietal Denomination: PER2009

(71) Applicant: Dana J. Groot, Encinitas, CA (US)

(72) Inventor: Dana J. Groot, Encinitas, CA (US)

(73) Assignee: Ecke Ranch B.V., De Lier (NL)

( * ) Notice: Subject to any disclaimer, the term of this patent is extended or adjusted under 35 U.S.C. 154(b) by 0 days.

(21) Appl. No.: 13/694,964

(22) Filed: Jan. 22, 2013

(51) Int. Cl.
*A01H 5/00* (2006.01)

(52) U.S. Cl.
USPC ..... Plt./303

(58) Field of Classification Search
USPC ..... Plt./303
See application file for complete search history.

*Primary Examiner* — Anne Grunberg
(74) *Attorney, Agent, or Firm* — C. A. Whealy

(57) ABSTRACT

A new and distinct cultivar of Poinsettia plant named 'PER2009', characterized by its relatively compact, uniform, upright and mounded plant habit; moderately vigorous growth habit; freely and upright branching habit; dark green-colored leaves; mid-season flowering response; under natural season conditions, plants flower in late November in Southern California; large inflorescences with light orange-colored flower bracts covered with rose pink-colored random speckles and splotches; and good post-production longevity.

1 Drawing Sheet

Botanical designation: *Euphorbia pulcherrima* Willd.
Cultivar denomination: 'PER2009'.

CROSS REFERENCED TO CLOSELY-RELATED APPLICATIONS

Title: Poinsettia Plant Named 'PER2109'
Applicant: Dana J. Groot
Filed: Concurrently with this application having U.S. Plant patent application Ser. No. 13/694,961.

BACKGROUND OF THE INVENTION

The present invention relates to a new and distinct cultivar of Poinsettia plant, botanically known as *Euphorbia pulcherrima* Willd., and hereinafter referred to by the name 'PER2009'.

The new Poinsettia plant originated is a naturally-occurring whole plant mutation of *Euphorbia pulcherrima* Willd. '490', disclosed in U.S. Plant Pat. No. 7,825. The new Poinsettia plant was discovered and selected by the Inventor as a single flowering plant from within a population of plants of '490' in a controlled greenhouse environment in Encinitas, Calif. in December, 2006.

Asexual reproduction of the new Poinsettia plant by terminal vegetative cuttings in a controlled greenhouse environment in Encinitas, Calif. since December, 2007 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER2009'. These characteristics in combination distinguish 'PER2009' as a new and distinct Poinsettia plant:

1. Relatively compact, uniform, upright and mounded plant habit.
2. Moderately vigorous growth habit.
3. Freely and upright branching habit.
4. Dark green-colored leaves.
5. Mid-season flowering response; under natural season conditions, plants flower in late November in Southern California.
6. Large inflorescences with light orange-colored flower bracts covered with rose pink-colored random speckles and splotches.
7. Good post-production longevity.

In side-by-side comparisons conducted in Encinitas, Calif., plants of the new Poinsettia differ primarily from plants of the parent, '490', in flower bract color as plants of '490' have dark red-colored flower bracts with no flecking. In addition, plants of the new Poinsettia are more compact than and not as vigorous as plants of '490'.

Plants of the new Poinsettia can be compared to plants of the *Euphorbia pulcherrima* Willd. 'PER2109', disclosed in U.S. Plant patent application Ser. No. 13/694,961. Plants of the new Poinsettia and 'PER2109' differ primarily in flower bract color.

Plants of the new Poinsettia can also be compared to plants of the *Euphorbia pulcherrima* Willd. '3-91', disclosed in U.S. Plant Pat. No. 9,602. In side-by-side comparisons conducted in Encinitas, Calif., plants of the new Poinsettia differed primarily from plants of '3-91' in the following characteristics:

1. Plants of the new Poinsettia were more compact than and not as vigorous as plants of '3-91'.
2. Leaves of plants of the new Poinsettia were darker green in color than leaves of plants of '3-91'.

3. Plants of the new Poinsettia flowered about one week earlier than plants of '3-91' when grown under natural season conditions.
4. Plants of the new Poinsettia and '3-91' differed in leaf and flower bract shape.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER2009' grown in a container.

The photograph at the top of the sheet is a close-up view of a typical flowering plant of 'PER2009'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 24° C., night temperatures averaged 17° C. and light levels ranged from 3,500 to 4,500 foot-candles. Measurements and numerical values represent averages for typical flowering plants. Plants were pinched one time and were 18 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER2009'.

Parentage: Naturally-occurring whole plant mutation of *Euphorbia pulcherrima* Willd. '490', disclosed in U.S. Plant Pat. No. 7,825.

Propagation:

*Type*.—Terminal vegetative cuttings.

*Time to initiate roots*.—About one to two weeks at 20° C. night temperature and 27° C. day temperature.

*Time to produce a rooted young plant*.—About four weeks at 16° C. night temperature and 18° C. day temperature.

*Root description*.—Fibrous; white in color.

Plant description:

*Plant habit and form*.—Relatively compact, uniform, upright and mounded plant habit; inverted triangle; large inflorescences positioned above the foliar plane; moderately vigorous growth habit.

*Plant height*.—About 31 cm.

*Plant diameter or spread*.—About 48 cm.

*Lateral branch description*.—Quantity: Freely branching habit, about eight lateral branches develop after pinching. Length: About 28 cm. Diameter: About 9 mm. Internode length: About 1.7 cm. Strength: Strong. Texture: Smooth, glabrous. Color: Close to 146B.

*Leaf description*.—Arrangement: Alternate, simple. Length: About 13.3 cm. Width: About 9.2 cm. Shape: Broadly lanceolate. Apex: Acuminate. Base: Rounded. Margin: Mostly entire. Aspect: Flat. Venation pattern: Pinnate, arcuate. Texture, upper surface: Smooth, glabrous. Texture, lower surface: Pubescent; prominent venation. Color: Developing leaves, upper surface: Close to N137B. Developing leaves, lower surface: Close to 137C. Fully expanded leaves, upper surface: Darker than 139A; venation, close to 137A. Fully expanded leaves, lower surface: Close to 137A; venation, close to 147C. Petiole: Length: About 6 cm. Diameter: About 4 mm. Texture, upper and lower surfaces: Smooth, glabrous. Color, upper surface: Close to 146B. Color, lower surface: Close to 146C.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Mid-season flowering response; under natural season conditions, plants typically flower in late November in Southern California; under artificial long nyctoperiod/short photoperiod conditions, plants flower about 8 to 8.5 weeks later.

*Post-production longevity*.—Good post-production longevity; plants of the new Poinsettia maintain good substance and flower bract color for about four weeks under interior conditions; inflorescences persistent.

*Inflorescence diameter*.—About 27 cm.

*Inflorescence height* (*depth*).—About 11 cm.

*Flower bracts*.—Quantity per inflorescence: About 18 to 19. Length, largest bracts: About 14.3 cm. Width, largest bracts: About 11.2 cm. Shape: Broadly lanceolate to elliptical. Apex: Acuminate. Base: Rounded. Margin: Entire. Texture, upper surface: Slightly rugose, glabrous. Texture, lower surface: Veins prominent, glabrous. Aspect: Mostly horizontal, apices point upright. Venation pattern: Pinnate, arcuate. Color: Developing or transitional bracts, upper surface: Ground color, close to 151D; along midvein, close to 141B; tinted with close to 37A. Developing or transitional bracts, lower surface: Ground color, close to 154D tinted with close to 29C. Fully expanded bracts, upper surface: Ground color, close to 29C to 29D; numerous random speckles and splotches, close to 39A to 39B; color does not fade with development; central bracts, close to 46B to 46C. Fully expanded bracts, lower surface: Ground color, close to 4B overlain with tints of close to 39B to 39C; color does not fade with development. Bract petiole: Length: About 2.8 cm. Diameter: About 3 mm. Texture, upper and lower surfaces: Smooth, glabrous. Color, upper and lower surfaces: Close to 145A.

*Cyathia*.—Quantity per corymb: About 12 to 15. Length: About 1 cm. Width: About 8 mm. Shape: Ovoid. Texture: Smooth, glabrous. Color, immature: Close to 144A. Color, mature: Close to 144A to 144B.

*Nectaries*.—Quantity per cyathium: One or two. Length: About 6 mm. Width: About 4 mm. Shape: Elongated oval. Texture: Smooth, glabrous. Color: Close to 12A.

*Peduncles*.—Length: About 3 mm. Diameter: About 2.5 mm. Strength: Strong. Aspect: Mostly upright to outwardly. Texture: Smooth, glabrous. Color: Close to 145A.

*Reproductive organs*.—Stamens: Quantity per cyathium: About three to five. Filament length: About 3.5 mm. Filament color: Close to 37C to 37D. Anther shape: Oval; bi-lobed. Anther length: About 1 mm. Anther color: Close to N34A. Amount of pollen: Scarce. Pollen color: Close to 9A. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER2009' as illustrated and described.

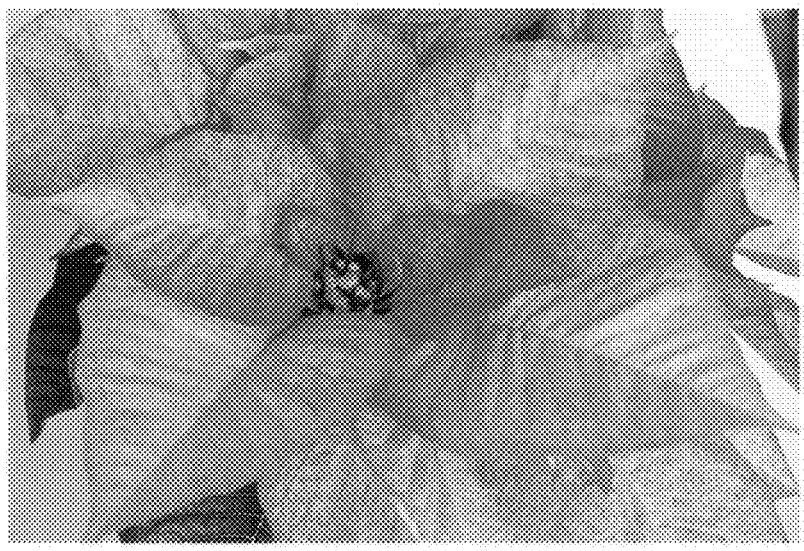
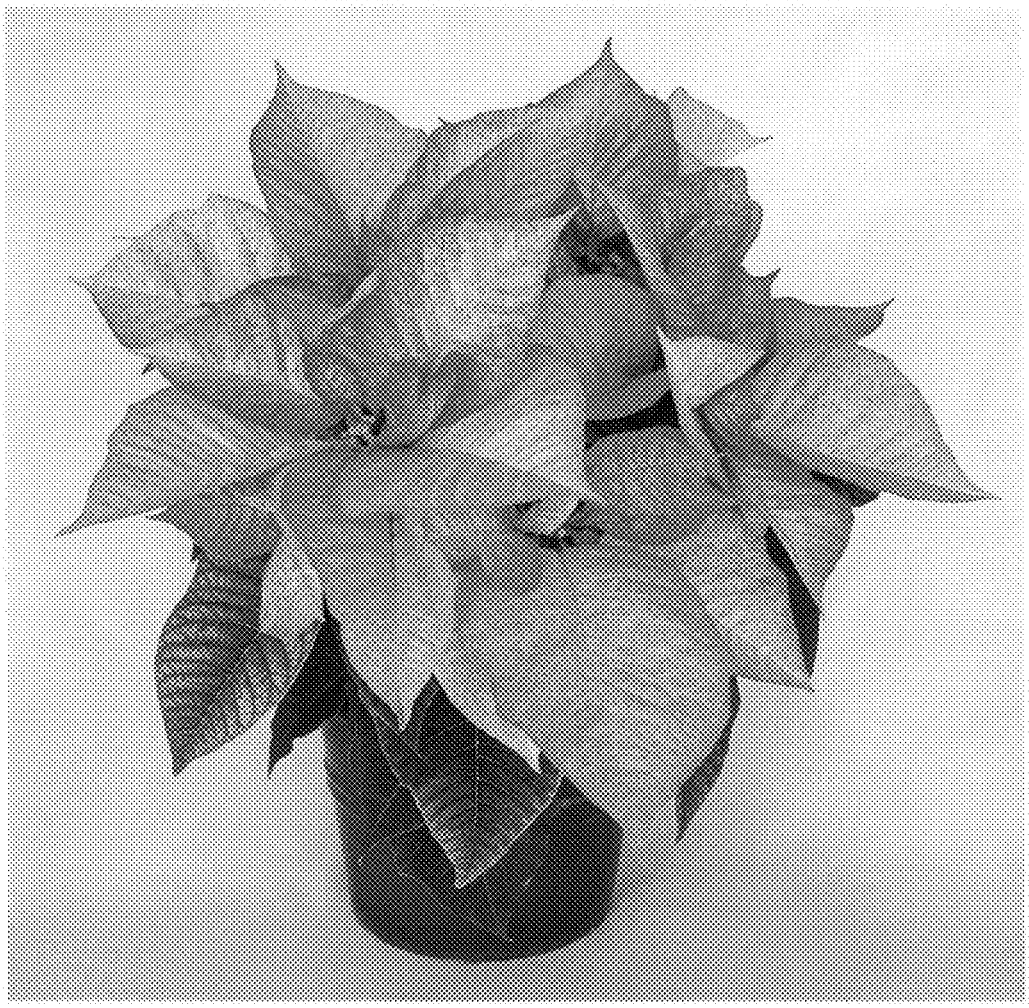

* * * * *